United States Patent
Miyata et al.

(10) Patent No.: US 6,916,792 B2
(45) Date of Patent: Jul. 12, 2005

(54) PROCESS FOR PREPARING ERYTHROMYCIN COMPOUND

(75) Inventors: Hiroyuki Miyata, Ube (JP); Akira Takama, Ube (JP); Tatsuya Kawaguchi, Ube (JP); Kazuma Sakata, Ube (JP); Kikuo Ataka, Ube (JP); Masayoshi Oku, Ube (JP); Hiroyuki Suenaga, Ube (JP)

(73) Assignees: UBE Industries, Ltd., Ube (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/480,272

(22) PCT Filed: Jun. 12, 2002

(86) PCT No.: PCT/JP02/05826

§ 371 (c)(1),
(2), (4) Date: Dec. 11, 2003

(87) PCT Pub. No.: WO02/102819

PCT Pub. Date: Dec. 27, 2002

(65) Prior Publication Data

US 2004/0192902 A1 Sep. 30, 2004

(30) Foreign Application Priority Data

Jun. 13, 2001 (JP) ........................................ 2001-178002

(51) Int. Cl.[7] .................... A61K 31/7048; A61K 31/70; C07H 17/08
(52) U.S. Cl. ............................ 514/29; 514/25; 536/7.2; 536/4.1; 536/18.5
(58) Field of Search ...................... 514/29, 25; 536/7.2, 536/4.1, 18.5

(56) References Cited

U.S. PATENT DOCUMENTS 5,959,088 A * 9/1999 Miura et al. ................. 536/7.2

FOREIGN PATENT DOCUMENTS

| EP | 0 846 697 A1 | 6/1998 |
|---|---|---|
| EP | 846697 A1 * | 6/1998 |
| EP | 0 884 322 A1 | 12/1998 |
| JP | 2-196796 A | 8/1990 |

OTHER PUBLICATIONS

New Current, vol. 7, No. 13, pp. 19–21 (Jun. 10, 1996).

* cited by examiner

*Primary Examiner*—James O. Wilson
*Assistant Examiner*—Michael C. Henry
(74) *Attorney, Agent, or Firm*—Birch, Stewart, Kolasch & Birch, LLP

(57) ABSTRACT

The present invention is to provide a process for producing a 2'-O-acetyl-4"-formyl-8,9-anhydroerythromycin A 6,9-hemiketal compound 4, and it provide a process for producing an erythromycin compound which comprises reacting a formylating agent with a 2'-O-acetylerythromycin A compound 2 to obtain 2-'-O-acetyl-4"-O-formylerythromycin A compound 3, then, acting an acid on Compound 3 to subject to hemiketalation, and then adding an aqueous basic solution in an aqueous solution to precipitate Compound 4 as free crystals.

14 Claims, No Drawings

PROCESS FOR PREPARING ERYTHROMYCIN COMPOUND

TECHNICAL FIELD

The present invention relates to a process for preparing an erythromycin compound.

BACKGROUND ART

Compound A (11-oxo-12-alkoxy-8,9-anhydroerythromycin A 6,9-hemiketal) which is an erythromycin compound represented by the formula:

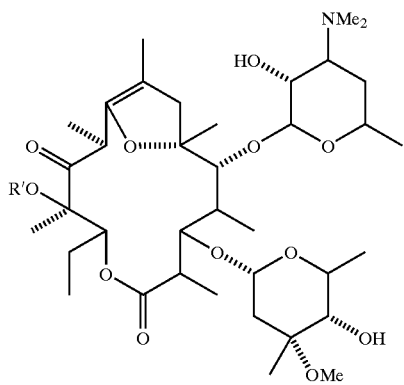

wherein R' represents a lower alkyl group, is a compound useful as a synthetic raw material of a gastro-prokinetic agent (for example, see de(N-methyl)-11-deoxy-N-isopropyl-12-O-methyl-11-oxo-8,9-anhydroxyerythromycin A 6,9-hemiacetal (GM-611), New Current 7(13), pp. 19–21, issued on Jun. 10, 1996). A method for producing the erythromycin compound has been already known. Of these, from erythromycin A represented by the formula:

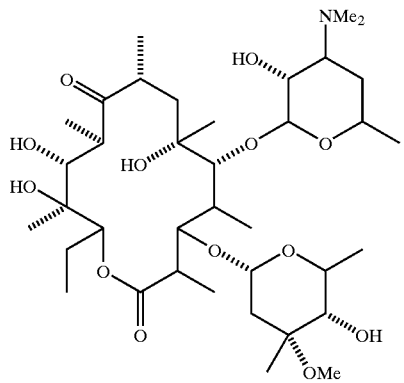

2'-O-acetylerythromycin A represented by the formula:

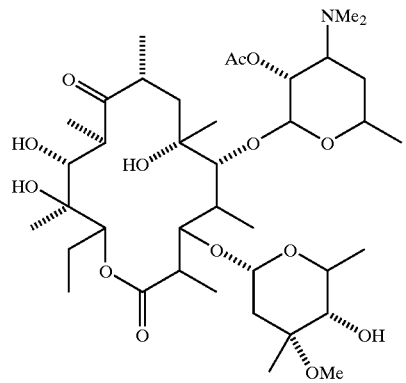

is obtained, and then, via 2'-O-acetyl-4"-O-formylerythromycin A represented by the formula:

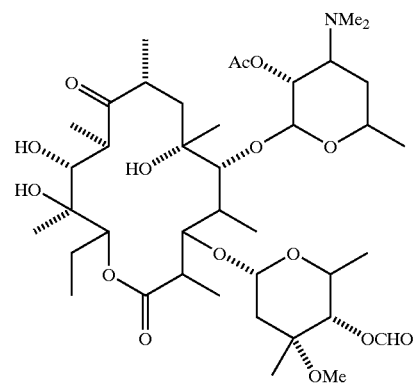

to produce 2'-O-acetyl-4"-O-formyl-8,9-anhydroerythromycin A 6,9-hemiketal represented by the formula:

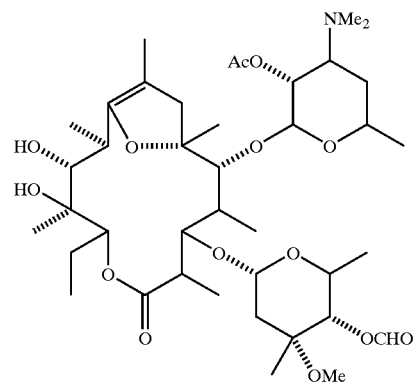

and finally the above-mentioned Compound A is obtaind as disclosed in Japanese Provisional Patent Publication No. 100291/1997 (which corresponds to U.S. Pat. No. 5,959,088). In this method, however, 11-O-formyl-2'-O-acetyl-4"-O-formylerythromycin A is by-produced in the formylation step, and the by-product is then transformed to a hemiketal form 11-O-formyl-2'-O-acetyl-4"-O-formyl-8,9-anhydroerythromycin A 6,9-hemiketal as a by-product. This by-product is extremely difficultly separated from an objective product, 2'-O-acetyl-4"-O-formyl-8,9-anhydroerythromycin A 6,9-hemiketal, so that there is a problem that the objective product can be difficultly obtained with a high purity. Thus, this method is not suitable for an industrial preparation method of a synthetic raw material of medical product required for purity specification or excellent quality.

To solve the above-mentioned problem, the present inventors have studied extensively to obtain a method of recovering 2'-O-acetyl-4"-O-formyl-8,9-anhydroerythromycin A 6,9-hemiketal which is a final objective product in a state of high purity with substantially not containing a by-product (11-O-formyl-2'-O-acetyl-4"-O-formyl-8,9-anhydroerythromycin A 6,9-hemiketal). As a result, they have found that after hemiketalation by reacting an acid which is after formylation in which a formylating agent is reacted with 2'-O-acetylerythromycin A compound, crystals are precipitated by adding an aqueous basic solution in an aqueous solution, then, crystals containing 2'-O-acetyl-4"-O-formyl-8,9-anhydroerythromycin A 6,9-hemiketal compound with high purity and substantially not containing a by-product can be obtained, whereby they have accomplished the present invention.

DISCLOSURE OF THE INVENTION

The present invention relates to a process for producing an erythromycin compound which is a 2'-O-acetyl-4"-O-formyl-8,9-anhydroerythromycin A 6,9-hemiketal compound (Compound 4) represented by the formula (4):

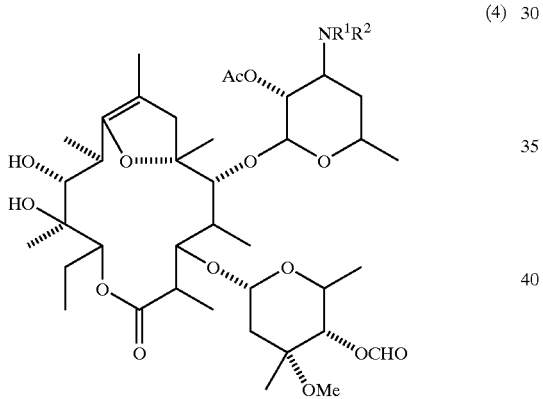

wherein $R^1$ and $R^2$ each independently represent a lower alkyl group, which comprises reacting a 2'-O-acetylerythromycin A compound (Compound 2) represented by the formula (2):

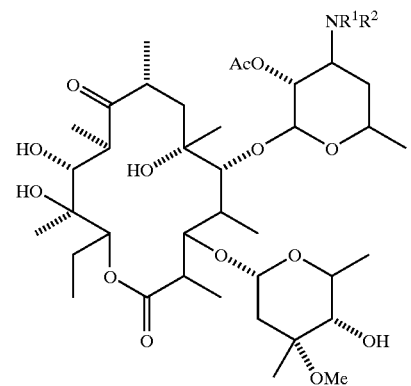

wherein $R^1$ and $R^2$ have the same meanings as defined above, with a formylating agent to obtain a 2'-O-acetyl-4"-O-formylerythromycin A compound (Compound 3) represented by the formula (3):

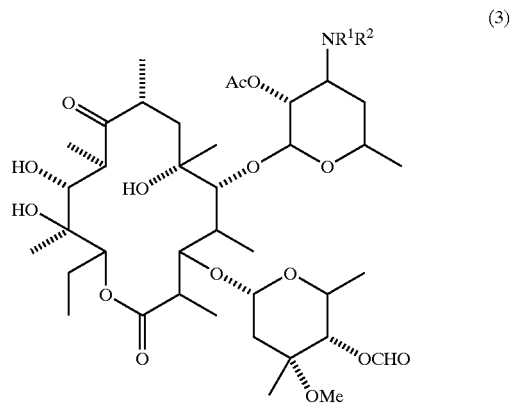

wherein $R^1$ and $R^2$ have the same meanings as defined above, then, reacting Compound 3 with an acid to subject to hemiketalation, and adding an aqueous basic solution in an aqueous solution to precipitate Compound 4 as free crystals.

The present invention also relates to a process further containing, in the above-mentioned process, a step of obtaining Compound 2 which is a starting compound by reacting an acetylating agent to the erythromycin A compound (Compound 1) represented by the formula (1):

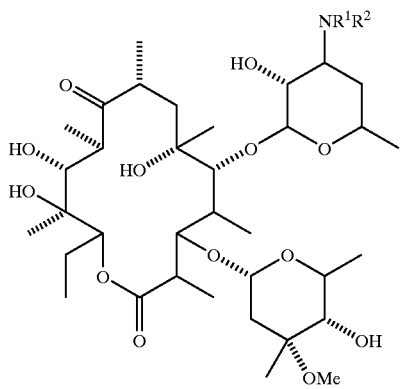

(1)

wherein $R^1$ and $R^2$ each independently represent a lower alkyl group, before reacting a formylating agent to Compound 2.

BEST MODE FOR CARRYING OUT THE INVENTION

The processes of the present invention mentioned above are shown together by the following reaction scheme.

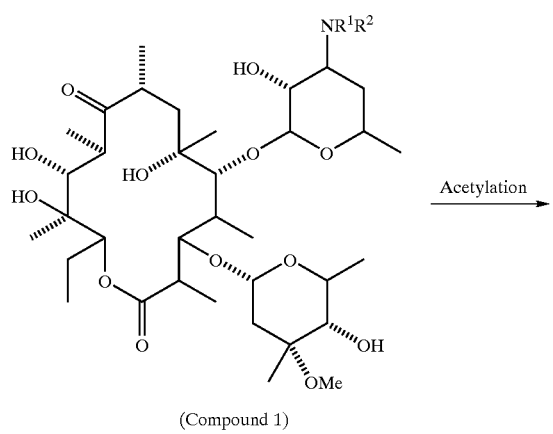

(Compound 1)

↓ Acetylation

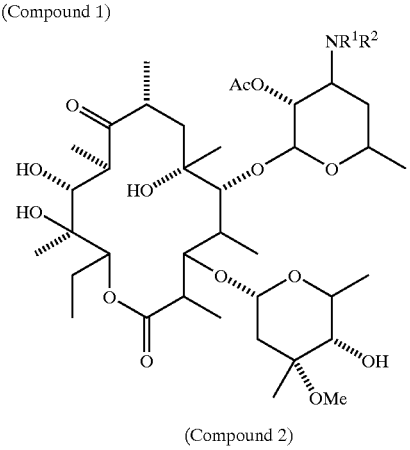

(Compound 2)

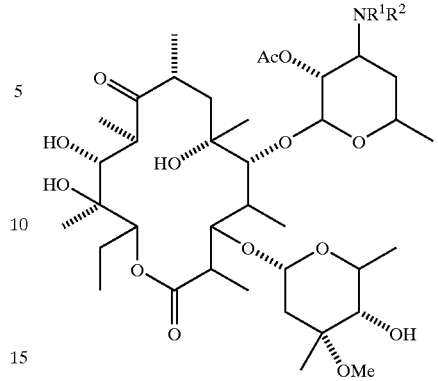

(Compound 2)

↓ Formylation step

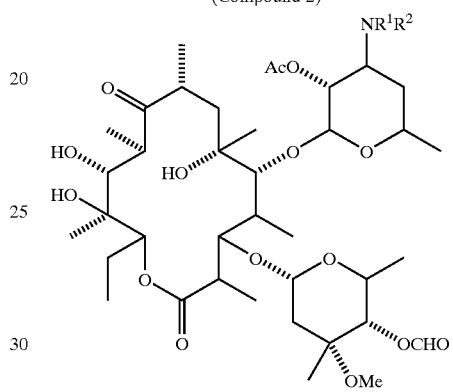

(Compound 3)

↓ Hemiketalation step

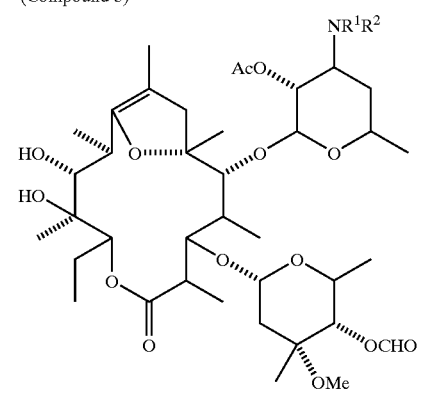

(Compound 4)

In the respective compounds to be used in the processes of the present invention, $R^1$ and $R^2$ each independently represent a lower alkyl group, and as the lower alkyl group, there may be specifically mentioned, for example, a straight or branched alkyl group having 1 to 4 carbon atoms such as a methyl group, an ethyl group, a n-propyl group, isopropyl group, a n-butyl group, an isobutyl group, a sec-butyl group, a tert-butyl group, etc., preferably a methyl group, an ethyl group, a n-propyl group, isopropyl group. Above all, the case where $R^1$ and $R^2$ are each a methyl group, and the case where $R^1$ is a methyl group and $R^2$ is an isopropyl group are preferably mentioned.

(A) Formylation Step

In the process of the present invention, a formylating agent is reacted with the above-mentioned 2'-O-acetyl-erythromycin A compound (Compound 2) to formylate the hydroxyl group at the 4"-position of Compound 2 to give Compound 3.

In the step of the formylation, as the formylating agent, an optional reagent can be used so long as it is an agent capable of introducing a formyl group into a hydroxyl group, and there may be mentioned, for example, a mixture of formic acid-acetic acid compound such as formic acid-acetic anhydride, sodium formate-acetyl chloride, etc., and 1-formylimidazole. It is preferably used a mixture of formic acid-acetic acid compound, more preferably formic acid-acetic anhydride. These formylating agents may be used singly or in combination of two or more in admixture. Incidentally, a mixture of formic acid-acetic acid compound may be used in the form of a mixture previously produced as a mixture and added, or separately added and mixed in the reaction system. With regard to a mixing ratio of the formic acids and the acetic acid compound at that time, optimum range may vary depending on the kinds of the formic acids and the acetic acid compound to be used, and for example, when formic acid-acetic anhydride is used, acetic anhydride is preferably used in an amount of about 0.5 to 1.0 mol based on 1 mol of formic acid, and when sodium formate-acetyl chloride is used, acetyl chloride is preferably used in an amount of about 1.0 to 2.0 mol based on 1 mol of sodium formate.

An amount of the above-mentioned formylating agent to be used is preferably about 1 to 10-fold mol, more preferably about 2 to 7-fold mol, particularly preferably about 4 to 6-fold mol based on the amount of Compound 2.

The formylation step is desirably carried out in the presence of a base to improve reaction rate. As the usable base, there may be preferably mentioned an organic base, for example, pyridines such as pyridine, 4-dimethylaminopyridine, etc.; tertiary amines such as triethylamine, etc.; secondary amines such as diethylamine, diisopropylamine, pyrrolidine, piperidine, morpholine, etc. It is particularly preferably used pyridine. These bases may be used singly or in combination of two or more in admixture.

An amount of the above-mentioned base to be used is preferably about 1.0 to 5.0-fold mol, more preferably about 1.0 to 1.5-fold mol based on the amount of Compound 2. Incidentally, when Compound 2 is a compound obtained by subjecting Compound 1 to acetylation in the presence of a base, and Compound 2 obtained by the step of the acetylation is applied as such to the reaction of formylation, the reaction may be carried out by not adding a base any more.

The formylation is preferably carried out in the presence of a solvent. The solvent to be used and an amount thereof are not specifically limited so long as it does not inhibit the reaction, and those which do not inhibit the reaction through all the steps of acetylation, formylation and hemiketalation can be suitably used. There may be mentioned, for example, carboxylic acid esters such as ethyl acetate, etc.; ketones such as acetone, etc.; halogenated aliphatic hydrocarbons such as dichloromethane, chloroform, etc., preferably ethyl acetate, acetone, more preferably ethyl acetate can be used. These solvents may be used singly or in combination of two or more in admixture.

An amount of the above-mentioned solvent can be optionally controlled depending on uniformity of the reaction solution or stirrability thereof, preferably 1,000 to 5,000 ml, more preferably 2,200 to 4,400 ml based on 1 mol of Compound 2. Incidentally, when Compound 2 is obtained by acetylating Compound 1 in a solvent and Compound 2 obtained in the step of the acetylation is applied as such to the reaction of the formylation, the reaction can be carried but in the same solvent to that used in the acetylation as a matter of course.

The formylation can be carried out by a method in which, for example, Compound 2 (when formylation is carried out directly after the acetylation as such, the resulting product may not be isolated or purified), a formylating agent, a base and a solvent are mixed under an atmosphere of an inert gas (for example, nitrogen, argon, helium, etc.), and reacted, and the like. A reaction temperature at that time is preferably about −40 to 5° C., more preferably −20 to 0° C., and a reaction pressure is not specifically limited. A reaction time is preferably about 7 hours.

Compound 3 obtained by the formylation step of the present invention may be applied to the next hemiketalation step by once isolating and purifying with a general method such as distillation, recrystallization, column chromatography, etc. after completion of the reaction, but it is more preferred to use Compound 3 without isolation and purification to carry out the formylation step and the hemiketalation step continuously in view of reaction operation.

(B) Hemiketalation Step

In the hemiketalation, Compound 3 subjected to formylation in the previous step is reacted with an acid whereby the hydroxyl group at the 6-position and the keto group at the 9-position are subjected to hemiketalation to prepare Compound 4, and then, an aqueous basic solution is added to the mixture in an aqueous solution to precipitate Compound 4 as crystals. According to this step, Compound 4 can be obtained as free crystals.

As the acid to be used in the hemiketalation, there may be preferably mentioned organic acid, for example, formic acid, acetic acid, propionic acid, etc., and formic acid can be particularly preferably used. These acids may be used singly or in combination of two or more kinds in admixture. Incidentally, the reaction may be carried out without further adding an acid when Compound 2 used as a stating compound in the previous formylation step is obtained by acetylating Compound 1 in the presence of an acid, and the formylation and hemiketalation steps are carried out continuously from the acetylation step, or when an acid such as formic acid, etc. is used in the formylation step, and the hemiketalation step is carried out continuously from the formylation step.

An amount of the above-mentioned acid is preferably about 2 to 100-fold mol, more preferably about 4 to 20-fold mol, particularly preferably about 5 to 15-fold mol based on the amount of Compound 3.

The hemiketalation is desirably carried out in the presence of a solvent, and the solvent to be used and an amount thereof are the same those described in the previous formylation. Incidentally, when Compound 2 used as a starting compound in the previous formylation step is obtained by acetylating Compound 1 in a solvent, and the formylation and hemiketalation are carried out continuously from the acetylation, or when a solvent is used in the formylation, and the hemiketalation is carried out continuously from the formylation, it can be carried out with the same solvent to those used in the acetylation or hemiketalation step as a matter of course.

As the aqueous basic solution to be added to precipitate Compound 4 as crystals after preparing Compound 4 by subjecting Compound 3 to hemiketalation with an acid, there may be preferably mentioned an aqueous basic solution of an inorganic base, for example, an aqueous alkali metal hydroxide solution such as an aqueous sodium hydroxide solution, an aqueous potassium hydroxide solution, etc.; an aqueous alkaline earth metal hydroxide solution such as an aqueous calcium hydroxide solution, an aqueous magnesium hydroxide solution, etc.; an aqueous alkali metal carbonate solution such as an aqueous sodium carbonate solution, an aqueous potassium carbonate solution, etc.; an aqueous alkali metal hydrogen carbonate solution such as an aqueous sodium hydrogen carbonate solution, an aqueous potassium hydrogen carbonate solution, etc. It is preferably used an aqueous sodium hydroxide solution, an aqueous potassium hydroxide solution, an aqueous sodium hydrogen carbonate solution, more preferably an aqueous sodium hydroxide solution, and an aqueous sodium hydrogen carbonate solution. These aqueous basic solutions may be used singly or in combination of two or more kinds in admixture. Incidentally, the aqueous basic solution may be added as a previously and separately prepared solution, or water and a base are separately added to prepare it in a reaction system. A concentration of the aqueous basic solution at that time is not specifically limited, and is preferably about 0.1 to 10 mol/L, more preferably about 1 to 7 mol/L.

An amount of the above-mentioned aqueous basic solution to be used is not specifically limited so long as it can make a pH of the reaction solution preferably about 6.5 to 10.0, more preferably about 7.0 to 9.0.

These hemiketalation and crystals-precipitating steps are carried out, for example, by mixing Compound 3 (which may not be isolated and purified), an acid and a solvent preferably at about 0 to 60° C., more preferably at about 20 to 50° C. for about 2 hours under an inert gas atmosphere (for example, nitrogen, argon, helium, etc.).

Thereafter, an aqueous basic solution is added so that a temperature of the reaction solution becomes preferably about −5 to 30° C., more preferably about 0 to 20° C., whereby Compound 4 is precipitated as free crystals. A reaction temperature and a reaction step at this step are not specifically limited. Incidentally, before adding the aqueous basic solution, the reaction solution is washed with water or an aqueous solution of an inorganic salt, so that an amount of the aqueous basic solution to be used may be lowered.

Compound 4 obtained by the above-mentioned hemiketalation step and precipitated as crystals can be isolated and purified by washing with water or an aqueous solution of an inorganic salt and drying, after completion of the reaction and after filtration thereof, and by carrying out the following purification step successively, Compound 4 having a higher purity can be obtained.

(C) Purification Step

In the purification step, Compound 4 obtained in the previous hemiketalation step and precipitated as crystals is dissolved in an organic solvent, washed with water or an aqueous solution of an inorganic salt and concentrated, and then, the concentrated solution is stirred under stirring in a saturated hydrocarbon solvent to recrystallized the compound, so that Compound 4 having a higher purity can be obtained.

As the organic solvent to be used in the purification step, it is not specifically limited so long as it can dissolve Compound 4, and there may be mentioned, for example, carboxylic acid esters such as ethyl acetate, etc.; aromatic hydrocarbons such as toluene, xylene, etc.; and halogenated aliphatic hydrocarbons such as methylene chloride, etc., preferably ethyl acetate and methylene chloride, more preferably ethyl acetate can be used.

An amount of the above-mentioned organic solvent is not specifically limited so long as it is an amount sufficient to completely dissolve Compound 4, and it is preferably about 1,500 to 60,000 ml, preferably about 9,000 to 30,000 ml based on mol of Compound 4. When Compound 2 obtained in the acetylation step of Compound 1 is applied as such to the reactions of formylation and the subsequent hemiketalation, it is preferably about 1,000 to 30,000 ml, more preferably about 5,000 to 15,000 ml based on 1 mol of Compound 1 used in the acetylation step.

In the purification step, as the aqueous solution of an inorganic salt to be used for washing a solution obtained by dissolving Compound 4 in an organic solvent, there may be preferably mentioned a neutral aqueous solution of an inorganic salt, and, for example, an aqueous sodium chloride solution, etc. may be used. Incidentally, a concentration of the aqueous solution of an inorganic salt is not specifically limited.

As the saturated hydrocarbon solvent which can be used for mixing with a solution of Compound 4 after washing as mentioned above and for stirring under heating, there may be preferably mentioned a straight, branched or cyclic saturated hydrocarbons having 5 to 12 carbon atoms, for example, pentane, hexane, heptane, octane, nonane, decane (those mentioned above all include various kinds of isomers), cyclopentane, cyclohexane, cyclopentane, etc., preferably hexane and cyclohexane, more preferably hexane may be used. These saturated hydrocarbon solvents may be used singly or in combination of two or more in admixture.

An amount of the above-mentioned saturated hydrocarbon solvent to be used is preferably about 900 to 38,000 ml, more preferably about 3,800 to 13,000 ml based on 1 mol of Compound 4 to be purified. When Compound 2 obtained in the acetylation step of Compound 1 is applied as such to the reactions of formylation and the subsequent hemiketalation, it is preferably about 500 to 20,000 ml, more preferably about 2,000 to 7,000 ml based on 1 mol of Compound 1 used in the acetylation step.

In the purification step, purification is carried out by dissolving Compound 4 which was obtained in the hemiketalation step and precipitated as crystals by adding an aqueous basic solution, in the above-mentioned organic solvent, washing with water or an aqueous solution of an inorganic salt, and concentrating the same until a volume of the solution becomes about 0.05 to 0.5-fold, and then, the concentrated solution is mixed with a saturated hydrocarbon solvent and the resulting solution is stirred preferably at about 35 to 100° C., more preferably at about 50 to 80° C. for about 0.5 hour under heating, and the like to carry out recrystallization. Incidentally, crystals of purified Compound 4 with higher purity can be easily isolated, after filtration, by washing and drying.

(D) Acetylation Step

As mentioned above, the process of the present invention relates to a process for preparing a 2'-O-acetyl-4"-O-formyl-8,9-anhydroerythromycin A 6,9-hemiketal compound (Compound 4) from a 2'-O-acetylerythromycin A compound (Compound 2) which is an erythromycin A compound in which the 2'-position is acetylated, and the Compound 2 can be obtained by reacting an acetylating agent to the erythromycin A compound (Compound 1) to acetylate the hydroxyl group at the 2'-position of Compound 1. Accordingly, the present invention is also relates to a process which further contains a step of obtaining Compound 2 of the formula (2) by reacting an acetylating agent with the erythromycin A compound (Compound 1) of the above-mentioned formula (1) before reacting the formylating agent with Compound 2 in the above-mentioned process of the present invention.

As the acetylating agent to be used in the acetylation step, there may be mentioned, for example, acetic anhydride; acetyl halide such as acetyl chloride, etc.; acetate such as sodium acetate; 1-acetylimidazole, and the like, preferably acetic anhydride and acetyl chloride, more preferably acetic anhydride can be used. These acetylating agent may be used singly or in combination of two or more in admixture.

An amount of the above-mentioned acetylating agent is preferably about 1.0 to 2.0-fold mol, more preferably about 1.0 to 1.5-fold mol, particularly preferably about 1.0 to 1.2-fold mol based on the amount of Compound 1.

The acetylation step is desirably carried out in the presence of a base to improve a reaction rate. As the base to be used, there may be preferably mentioned an organic base, for example, pyridines such as pyridine, 4-dimethylaminopyridine, etc.; tertiary amines such as triethylamine, etc.; secondary amines such as diethylamine, diisopropylamine, pyrrolidine, piperidine, morpholine, etc., and particularly preferably pyridine can be used. These bases may be used singly or in combination of two or more in admixture.

An amount of the above-mentioned base is preferably about 1.0 to 5.0-fold mol, more preferably about 1.0 to 1.5-fold mol based on the amount of Compound 1.

The acetylation step is desirably carried out in the presence of a solvent. As the solvent which can be used, it is not specifically limited so long as it does not inhibit the reaction, and preferably those which do not inhibit the reactions in all the steps of the acetylation step, and the formylation step and hemiketalation step carried out subsequent thereto are preferably used. Such a solvent may be mentioned, for example, carboxylic acid esters such as ethyl acetate, etc.; ketones such as acetone, etc.; halogenated aliphatic hydrocarbons such as dichloromethane, chloroform, etc., preferably ethyl acetate and acetone, more preferably ethyl acetate can be used. These solvents may be used singly or in combination of two or more in admixture.

An amount of the above-mentioned solvent to be used can be optionally controlled depending on uniformity of the reaction solution or stirability of the same, and preferably about 1,000 to 5,000 ml, more preferably about 2,200 to 4,400 ml based on 1 mol of Compound 1.

The acetylation step can be carried out, for example, in an atmosphere of an inert gas (for example, nitrogen, argon, helium, etc.), by mixing Compound 1, the acetylating agent, the base and the solvent and reacted these, and the like. A reaction temperature at that time is preferably about 0 to 50° C., more preferably 10 to 30° C., a reaction time is about one hour, and a reaction pressure is not specifically limited.

Compound 2 obtained by the acetylation step can be used in the subsequent formylation step of the present invention after once isolating and purifying it by a general method such as distillation, recrystallization, column chromatography, etc., after completion of the reaction. However, it is preferred to use Compound 2 without isolation and purification to carry out the acetylation step and the formylation step successively in view of reaction operation.

As mentioned above, the process of the present invention relates to a process for precipitating the objective compound as higher purity free crystals by adding an aqueous basic solution to the 2'-O-acetyl-4"-O-formyl-8,9-anhydroerythromycin A 6,9-hemiketal compound (Compound 4) in an aqueous solution obtained by formylation and hemiketalation, which is starting from the 2'-O-acetyl-erythromycin A compound (Compound 2) which is an erythromycin A compound in which the 2'-position is acetylated. Among the steps of the process of the present invention, a process of isolating and purifying the compound which is to precipitate the compound from an aqueous solution containing Compound 4 as higher purity free crystals by adding an aqueous basic solution can be made a part of the present invention. Accordingly, the present invention also relates to a process of isolating and purifying a 2'-O-acetyl-4"-O-formyl-8,9-anhydroerythromycin A 6,9-hemiketal compound represented by the formula (4):

wherein $R^1$ and $R^2$ each independently represent a lower alkyl group, which comprises adding a basic solution to an aqueous solution containing the compound and impurities to precipitate the compound from the aqueous solution as free crystals. According to the present process, in addition to the 2'-O-acetyl-4"-O-formyl-8,9-anhydroerythromycin A 6,9-hemiketal compound produced through a role of steps as mentioned above, the 2'-O-acetyl-4"-O-formyl-8,9-anhydroerythromycin A 6,9-hemiketal compound is selectively precipitated from a reaction mixture containing various kinds of by-products which are difficultly isolated to give higher purity crystals of the compound.

Incidentally, the erythromycin A compound of the formula (1) to be used for obtaining the compound of the formula (2) which is used as a starting compound of the process of the present invention can be prepared according to the method disclosed in Japanese Provisional Patent Publication No. 100291/1997 (which corresponds to U.S. Pat. No. 5,959,088), and a method known in this field of the art.

EXAMPLE

Next, the present invention is specifically explained by referring to Examples and Comparative examples, but the scope of the present invention is not limited by these.

Example 1

To a flask having an inner volume of 20,000 ml equipped with a stirring device, a thermometer and a dropping funnel were charged 1000 g (1.36 mol) of erythromycin A (Compound 1, obtained according to the method disclosed in Japanese Provisional Patent Publication No. 100291/1997), 167 g (1.64 mol) of acetic anhydride, 172 g (2.18 mol) of pyridine and 4,000 ml of ethyl acetate, and the mixture was reacted at 20 to 30° C. for one hour. Thereafter, a mixture of 564 g (12.3 mol) of formic acid and 626 g (6.13 mol) of acetic anhydride was added to the above mixture and reacted at −5° C. for 8 hours, at 10° C. for 3 hours, and at 50° C. for 2 hours.

After completion of the reaction, while maintaining a liquid temperature of the reaction solution to 10° C., 3,000 ml of water, and 3730 ml (22.4 mol) of a 6 mol/L aqueous sodium hydroxide solution were added to the mixture in this order to adjust a pH of the reaction solution to 7.0 to 7.5. Moreover, 30 g (0.36 mol) of sodium hydrogen carbonate was added to the mixture to adjust a pH of the reaction solution to 7.4 to 7.7 and the mixture was stirred at −5 to 15° C. for 2 hours to precipitate free crystals. The obtained crystals were collected by filtration to obtain 718 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 97.4% (areal percentage). Incidentally, an existence ratio of Compound 4 and a by-product (11-formyl-2'-O-acetyl-4"-O-formyl-8,9-anhydroerythromycin A 6,9-hemiketal) was 98.6:1.4.

Subsequently, the above-mentioned white crystals were dissolved in 11,110 ml of ethyl acetate, and then, washed with 1,100 g of a 15% by weight aqueous sodium chloride solution, the organic layer was taken out and dried over anhydrous magnesium sulfate. After filtration, the mixture was concentrated under reduced pressure, the concentrated solution and 6,800 ml of n-hexane were mixed, and the mixture was stirred under reflux (67° C.) for 30 minutes, and after cooling to room temperature and adding 1,200 ml of ethyl acetate, further at 0 to 5° C. for one hour. The obtained crystal was filtered and dried to give 519 g of Compound 4 (Isolated yield based on Compound 1: 48%) as white crystals with a purity of 97.4% (areal percentage according to high performance liquid chromatography, analytical condition 1).

Incidentally, physical properties of Compound 4 were as follows.

Melting point; 233 to 236° C.

$^1$H-NMR (CDCl$_3$, δ (ppm)); 0.89 (3H, t, J=7.3 Hz), 0.94 (3H, d, J=7.8 Hz), 1.55 (3H, s), 2.05 (3H, s), 2.27 (6H, s), 3.36 (3H, s), 4.62 (1H, d, J=7.3 Hz), 4.86 (1H, dd, J=1.1, 2.4 Hz), 5.16 (1H, d, J=4.9 Hz), 8.20 (1H, d, J=1.0 Hz)

Example 2

To a flask having an inner volume of 1,000 ml equipped with a stirring device, a thermometer and a dropping funnel were charged 50 g (68 mmol) of erythromycin A (Compound 1), 8.4 g (82 mmol) of acetic anhydride, 8.6 g (110 mmol) of pyridine and 200 ml of ethyl acetate, and the mixture was reacted at 20 to 30° C. for one hour. Thereafter, a mixture of 28.2 g (610 mmol) of formic acid and 31.3 g (310 mmol) of acetic anhydride was added to the resulting mixture and the thus obtained mixture was reacted at −5° C. for 7 hours, at 10° C. for 14 hours, and at 50° C. for 2 hours.

After completion of the reaction, while maintaining the liquid temperature of the reaction solution to 10° C., 150 ml of water, and 184 ml (1.1 mol) of a 6 mol/L aqueous sodium hydroxide solution were added to the solution in this order to adjust a pH of the reaction solution to 7.0 to 7.7. Moreover, 1.5 g (18 mmol) of sodium hydrogen carbonate was added to the mixture to adjust a pH of the reaction solution to 7.5 to 8.6, and the mixture was stirred at −5 to 15° C. for 2 hours to precipitate free crystals. The obtained crystals were collected by filtration to obtain 28.9 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 96.2% (areal percentage). Incidentally, an existence ratio of Compound 4 and a by-product (11-O-formyl-2'-O-acetyl-4"-O-formyl-8,9-anhydroerythromycin A 6,9-hemiketal) was 98.2:1.8.

Example 3

To a flask having an inner volume of 1,000 ml equipped with a stirring device, a thermometer and a dropping funnel were charged 100 g (140 mmol) of erythromycin A (Compound 1), 16.7 g (160 mmol) of acetic anhydride, 17.2 g (220 mmol) of pyridine and 400 ml of ethyl acetate, and the mixture was reacted at 20 to 30° C. for one hour. Thereafter, a mixture of 56.4 g (1,230 mmol) of formic acid and 62.6 g (620 mmol) of acetic anhydride was added to the above mixture, and the resulting mixture was reacted at −5 to 0° C. for 8 hours, at 10 to 15° C. for for one hour, and at 40 to 50° C. for 2 hours.

After completion of the reaction, the reaction mixture was divided into two portions (hereinafter referred to as Reaction mixture A and Reaction mixture B, respectively).

While maintaining a liquid temperature of Reaction mixture A to 10° C., 150 ml of water, and 182 ml (1.1 mol) of a 6 mol/L aqueous sodium hydroxide solution were added to the mixture in this order to adjust a pH of the reaction solution to 7.46. Moreover, 1.5 g (18 mmol) of sodium hydrogen carbonate was added to the mixture to adjust a pH of the reaction solution to 7.8 to 8.1, and the mixture was stirred at −5 to 15° C. for 3 hours to precipitate free crystals. The obtained crystals were collected by filtration to obtain 33.8 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 96.6% (areal percentage). Incidentally, an existence ratio of Compound 4 and a by-product (11-O-formyl-2'-O-acetyl-4"-O-formyl-8,9-anhydroerythromycin A 6,9-hemiketal) was 98.4:1.6.

Subsequently, the above-mentioned white crystals were dissolved in 555 ml of ethyl acetate, the solution was washed twice with each 50 ml of a 15% by weight aqueous sodium chloride solution, and the organic layer was taken out and dried over anhydrous magnesium sulfate. After filtration, the mixture was concentrated under reduced pressure, the concentrated solution and 340 ml of n-hexane were mixed, and the resulting mixture was stirred under reflux (67° C.) for 30 minutes, and after cooling to room temperature and adding 60 ml of ethyl acetate, further at 0 to 5° C. for one hour. The obtained crystals were filtered and dried to give 26.0 g of Compound 4 (Isolated yield based on Compound 1: 24%) as white crystals with a purity of 97.4% (areal percentage according to high performance liquid chromatography, analytical condition 1).

While maintaining a liquid temperature of Reaction mixture B to 10° C., 150 ml of water, and 180 ml (1.1 mol) of a 6 mol/L aqueous sodium hydroxide solution were added to the mixture in this order to adjust a pH of the reaction solution to 7.47. Moreover, 1.5 g (18 mmol) of sodium hydrogen carbonate was added to the mixture to adjust a pH of the reaction solution to 7.5 to 8.0, and the mixture was stirred at −5 to 0° C. for one hour to precipitate free crystals. The obtained crystals were collected by filtration to obtain 29.0 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 96.9% (areal percentage). Incidentally, an existence ratio of Compound 4 and a by-product (11-O-formyl-2'-O-acetyl-4"-O-formyl-8,9-anhydroerythromycin A 6,9-hemiketal) was 98.5:1.5.

Subsequently, the above-mentioned white crystals were dissolved in 555 ml of ethyl acetate, the solution was washed twice with each 50 ml of a 15% by weight aqueous sodium chloride solution, and the organic layer was taken out and dried over anhydrous magnesium sulfate. After filtration, the mixture was concentrated under reduced pressure, the concentrated solution and 340 ml of n-hexane were mixed, and the resulting mixture was stirred under reflux (67° C.) for 30 minutes, and after cooling to room temperature and adding 60 ml of ethyl acetate, further at 0 to 5° C. for one hour. The obtained crystals were filtered and dried to give 21.0 g of Compound 4 (Isolated yield based on Compound 1: 20%) as white crystals with a purity of 97.9% (areal percentage according to high performance liquid chromatography, analytical condition 1).

Example 4

To a flask having an inner volume of 1,000 ml equipped with a stirring device, a thermometer and a dropping funnel were charged 100 g (140 mmol) of erythromycin A (Compound 1), 16.7 g (160 mmol) of acetic anhydride, 17.2 g (220 mmol) of pyridine and 400 ml of ethyl acetate, and the mixture was reacted at 20 to 30° C. for one hour. Thereafter, a mixture of 56.4 g (1230 mmol) of formic acid and 62.6 g (620 mmol) of acetic anhydride was added to the above mixture, and the resulting mixture was stirred at −10 to 5° C. for 8.5 hours, at 11° C. for 14.5 hours, and at 40 to 50° C. for 2 hours.

After completion of the reaction, the reaction mixture was divided into two portions (hereinafter referred to as Reaction mixture A and Reaction mixture B, respectively).

While maintaining a liquid temperature of Reaction mixture A to 10° C., 150 ml of water, and 183.5 ml (1.1 mol) of a 6 mol/L aqueous sodium hydroxide solution were added to the mixture in this order to adjust a pH of the reaction solution to 8.10. Moreover, 1.5 g (18 mmol) of sodium hydrogen carbonate was added to the mixture to adjust a pH of the reaction solution to 8.3 to 8.4, and the mixture was stirred at −5 to 15° C. for 2 hours to precipitate free crystals. The obtained crystals were collected by filtration to obtain 33.8 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 96.1% (areal percentage). Incidentally, an existence ratio of Compound 4 and a by-product (11-O-formyl-2'-O-acetyl-4"-O-formyl-8,9-anhydroerythromycin A 6,9-hemiketal) was 98.1:1.9.

Subsequently, the above-mentioned white crystals were dissolved in 555 ml of ethyl acetate, the solution was washed twice with each 100 ml of a saturated aqueous sodium chloride solution, and the organic layer was taken out and dried over anhydrous magnesium sulfate. After filtration, the mixture was concentrated under reduced pressure, the concentrated solution and 340 ml of n-hexane were mixed, and the resulting mixture was stirred under reflux (67° C.) for 30 minutes, and after cooling to room temperature and adding 340 ml of ethyl acetate, further at 0 to 5° C. for one hour. The obtained crystals were filtered and dried to give 25.7 g of Compound 4 (Isolated yield based on Compound 1: 24%) as white crystals with a purity of 97.1% (areal percentage according to high performance liquid chromatography, analytical condition 1).

While maintaining a liquid temperature of Reaction mixture B to 10° C., 150 ml of water, and 181.6 ml (1.1 mol) of a 6 mol/L aqueous sodium hydroxide solution were added to the mixture in this order to adjust a pH of the reaction solution to 7.08. Moreover, 1.5 g (18 mmol) of sodium hydrogen carbonate was added to the mixture to adjust a pH of the reaction solution to 7.6 to 7.7, and the mixture was stirred at −5 to 15° C. for 2 hours to precipitate free crystals. The obtained crystals were collected by filtration to obtain 34.0 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 96.3% (areal percentage). Incidentally, an existence ratio of Compound 4 and a by-product (11-O-formyl-2'-C-acetyl-4"-O-formyl-8,9-anhydroerythromycin A 6,9-hemiketal) was 98.2:1.8.

Subsequently, the above-mentioned white crystals were dissolved in 555 ml of ethyl acetate, the solution was washed twice with each 100 ml of a saturated aqueous sodium chloride solution, and the organic layer was taken out and dried over anhydrous magnesium sulfate. After filtration, the mixture was concentrated under reduced pressure, the concentrated solution and 340 ml of n-hexane were mixed, and the resulting mixture was stirred under reflux (67° C.) for 30 minutes, and after cooling to room temperature and adding 60 ml of ethyl acetate, further at 0 to 5° C. for one hour. The obtained crystals were filtered and dried to give 26.1 g of Compound 4 (Isolated yield based on Compound 1: 24%) as white crystals with a purity of 97.3% (areal percentage according to high performance liquid chromatography, analytical condition 1).

Example 5

To a flask having an inner volume of 10,000 ml equipped with a stirring device, a thermometer and a dropping funnel were charged 1,041 g (1.42 mol) of erythromycin A (Compound 1), 174 g (1.70 mol) of acetic anhydride, 179 g (2.18 mol) of pyridine and 4,164 ml of ethyl acetate, and the mixture was reacted at 20 to 30° C. for one hour. Thereafter, a mixture of 588 g (12.7 mol) of formic acid and 652 g (6.39 mol) of acetic anhydride was added to the above mixture, and the resulting mixture was reacted at −5 to 0° C. for 9 hours, at 10 to 20° C. for 12 hours, and at 40 to 50° C. for 3 hours.

After completion of the reaction, while maintaining a liquid temperature of the reaction mixture to 30° C., the reaction mixture was washed with 2,082 ml of a 3% by weight aqueous sodium chloride solution, and 2,082 ml of a 10% by weight aqueous sodium chloride solution in this order, 2,600 ml of water, 1,650 ml (12.4 mol) of a 7.5 mol/L aqueous sodium hydroxide solution was added to the mixture in this order to adjust a pH of the reaction solution to 7.0 to 7.7. Moreover, 30 g (36 mmol) of sodium hydrogen carbonate was added to the mixture to adjust a pH of the reaction solution to 7.8 to 8.2, and the resulting mixture was stirred at 0 to 10° C. for one hour to precipitate free crystals. The obtained crystals were collected by filtration to obtain 930 g of white crystals. When the crystals were analyzed by high performance liquid chromatography (analytical condition 1), a purity of the objective 2'-O-acetyl-4"-O-formyl-8,9-anhydroerythromycin A 6,9-hemiketal (Compound 4) was 94.8% (areal percentage). Incidentally, an existence ratio of Compound 4 and a by-product (11-O-formyl-2'-O-acetyl-4"-O-formyl-8,9-anhydroerythromycin A 6,9-hemiketal) was 98.3:1.7.

Subsequently, the above-mentioned white crystals was dissolved in 13,849 ml of ethyl acetate, the solution was washed twice with each 1,250 g of a saturated aqueous sodium chloride solution, and the organic layer was taken out and dried over anhydrous magnesium sulfate. After filtration, the mixture was concentrated under reduced pressure, the concentrated solution and 7,079 ml of n-hexane were mixed and the resulting mixture was stirred under reflux (67° C.) for 30 minutes, and after cooling to room temperature and adding 1,249 ml of ethyl acetate, further at 0 to 5° C. for one hour. The obtained crystals were filtered and dried to give 592 g of Compound 4 (Isolated yield based on Compound 1: 53%) as white crystals with a purity of 97.3% (areal percentage according to high performance liquid chromatography, analytical condition 1). Reference example 1 (Synthesis of unpurified 2'-O-acetyl-4"-O-formyl-8,9-anhydroerythromycin A 6,9-hemiketal (Compound 4)).

To a flask having an inner volume of 3,000 ml equipped with a stirring device, a thermometer and a dropping funnel where charged 300 g (409 mmol) of erythromycin A (Compound 1), 50.4 g (494 mmol) of acetic anhydride, 51.8 g (655 mmol) of pyridine and 1,200 ml of ethyl acetate, and the mixture was reacted at 20 to 30° C. for one hour. Thereafter, a mixture of 169.3 g (3.68 mol) of formic acid and 188.3 g (1.84 mol) of acetic anhydride was added to the above mixture, and the resulting mixture was reacted at 0 to 5° C. for 3 hours, at 10 to 20° C. for 12 hours, and at 40 to 50° C. for 3 hours.

After completion of the reaction, while maintaining a liquid temperature of the reaction mixture to 20° C., 900 ml of water, and 1,125 ml (6.75 mol) of a 6 mol/L aqueous sodium hydroxide solution were added to the mixture in this order to adjust a pH of the reaction solution to 7.7. Moreover, 10 g (119 mmol) of sodium hydrogen carbonate was added to the reaction solution to adjust a pH of the same to 7.9 to precipitate free crystals. The reaction solution was filtered to separate it to crystals and a mother liquor. With respect to the mother liquor, after separating the aqueous layer, the organic layer was washed twice with each 615 ml of a saturated aqueous sodium chloride solution. Also, the crystals were dissolved in 3,330 ml of ethyl acetate, and the solution was washed twice with each 615 ml of a saturated aqueous sodium chloride solution. The organic layer was taken out and combined with the above-mentioned mother liquor, and the mixture was dried over anhydrous magnesium sulfate. After filtration, the filtrate was concentrated under reduced pressure, the concentrated solution and 2,055 ml of n-hexane were mixed and the resulting mixture was stirred under reflux (67° C.) for 30 minutes, and after cooling to room temperature and adding 360 ml of ethyl acetate, further at 0 to 5 C for one hour. The obtained crystals were filtered and dried to obtain 236 g of white crystals (Isolated yield based on Compound 1: 73%). When the crystals were analyzed by high performance liquid chromatography (analytical condition 1), a purity of unpurified 2'-O-acetyl-4"-O-formyl-8,9-anhydroerythromycin A 6,9-hemiketal (Compound 4) was a purity of 91.1% (areal percentage, analytical condition 1). Incidentally, an existence ratio of Compound 4 and a by-product (11-O-formyl-2'-O-acetyl-4"-O-formyl-8,9-anhydroerythromycin A 6,9-hemiketal) was 94.6:5.4.

Example 6

To a flask having an inner volume of 200 ml equipped with a stirring device, a thermometer and a dropping funnel were charged 8.0 g (10 mmol) of unpurified 2'-O-acetyl-4"-O-formyl-8,9-anhydroerythromycin A 6,9-hemiketal (Compound 4) obtained in Reference example 1, 40 ml of ethyl acetate and 60 ml of water, and the mixture was stirred at 0 to 10° C. To the mixture was added 0.56 g (12 mmol) formic acid at the same temperature, and then, 6.5 ml (19.5 mmol) of a 3 mol/L aqueous sodium hydroxide solution was added thereto to adjust a pH of the reaction solution to 6.2 to 7.9. The mixture was stirred at 0 to 10° C. for one hour, and crystals were collected by filtration and dried to give 5.9 g of Compound 4 (Isolated yield based on unpurified Compound 4: 74%) as white crystals with a purity of 96.4% (areal percentage according to high performance liquid chromatography, analytical condition 1). Incidentally, an existence ratio of Compound 4 and a by-product (11-O-formyl-2'-O-acetyl-4"-O-formyl-8,9-anhydroerythromycin A 6,9-hemiketal) was 98.5:1.5.

Example 7

To a flask having an inner volume of 200 ml equipped with a stirring device, a thermometer and a dropping funnel were charged 16.0 g (20 mmol) of unpurified 2'-O-acetyl-4"-O-formyl-8,9-anhydroerythromycin A 6,9-hemiketal (Compound 4) obtained in Reference example 1, 80 ml of ethyl acetate and 60 ml of water, and the mixture was stirred at 0 to 10° C. To the mixture was added 1.12 g (24 mmol) of formic acid at the same temperature, and then, 4.0 ml (24 mmol) of a 6 mol/L aqueous sodium hydroxide solution was added thereto to adjust a pH of the reaction solution to 9.4. The mixture was stirred at 0 to 10° C. for one hour, and crystals were collected by filtration and dried to give 10.0 g of Compound 4 (Isolated yield based on unpurified Compound 4: 63%) as white crystals with a purity of 95.9% (areal percentage according to high performance liquid chromatography, analytical condition 1). Incidentally, an existence ratio of Compound 4 and a by-product (11-O-formyl-2'-O-acetyl-4"-O-formyl-8,9-anhydroerythromycin A 6,9-hemiketal) was 98.0:2.0.

Example 8

To a flask having an inner volume of 200 ml equipped with a stirring device, a thermometer and a dropping funnel were charged 12.0 g (20 mmol) of unpurified 2'-O-acetyl-4"-O-formyl-8,9-anhydroerythromycin A 6,9-hemiketal (Compound 4) obtained in Reference example 1, 60 ml of ethyl acetate and 90 ml of water, and the mixture was stirred at 0 to 10° C. To the mixture were added 22.5 g (331 mmol) of sodium formate and 2.46 g (53 mmol) of formic acid at the same temperature, and then, 15 ml (45 mmol) of a 3 mol/L aqueous sodium hydroxide solution was added thereto to adjust a pH of the reaction solution to 7.7. The mixture was stirred at 0 to 10° C. for one hour, and crystals were collected by filtration and dried to give 8.8 g of Compound 4 (Isolated yield based on unpurified Compound 4: 73%) as white crystals with a purity of 95.5% (areal percentage according to high performance liquid chromatography, analytical condition 1). Incidentally, an existence ratio of Compound 4 and a by-product (11-O-formyl-2'-O-acetyl-4"-O-formyl-8,9-anhydroerythromycin A 6,9-hemiketal) was 97.8:2.2.

Comparative Example 1

According to the method described in Japanese Provisional Patent Publication No. Hei. 9-100291, 2'-O-acetyl-4"-O-formyl-8,9-anhydroerythromycin A 6,9-hemiketal (Compound 4) was prepared. To a flask having an inner volume of 300 ml equipped with a stirring device, a thermometer and a dropping funnel were charged 20.44 g (27.8 mmol) of erythromycin A (Compound 1), 3.41 g (33.4 mmol) of acetic anhydride, 3.53 g (44.6 mmol) of pyridine and 82 ml of ethyl acetate, and the mixture was reacted at 20 to 30° C. for one hour. Thereafter, while maintaining the reaction solution to 0° C., a mixture of 11.54 g (251 mmol) of formic acid and 12.8 g (125 mmol) of acetic anhydride was added to the mixture, and the resulting mixture was reacted as such for 3 hours, and after allowing to stand at room temperature overnight, it was reacted at 40 to 50° C. for 2 hours.

After completion of the reaction, 123 ml of ethyl acetate was added to the mixture, and the mixture was washed with 123 ml of ice-water. The organic layer was separated and neutralized by adding 123 ml (136 mmol) of a saturated aqueous sodium hydrogen carbonate solution and 14.0 g (167 mmol) of sodium hydrogen carbonate (pH=6.5).

The organic layer was again separated, washed three times with each 41 ml of a saturated aqueous sodium chloride solution, 30 ml of ethyl acetate was added to the organic layer, and further the organic layer was washed with 41 ml of a saturated aqueous sodium chloride solution. The aqueous layer after neutralization was extracted with 70 ml of ethyl acetate, and combined with the previous organic layer and the mixture was dried over anhydrous magnesium sulfate. After filtration, the filtrate was concentrated under reduced pressure, and the concentrated solution and 139 ml of n-hexane were mixed. The mixture was stirred under reflux (67° C.) for 30 minutes, and after cooling to room temperature and adding 25 ml of ethyl acetate, further at 0° C. for one hour. The obtained crystals were filtered and dried to give 15.55 g of white crystals. When the crystals were analyzed by high performance liquid chromatography (analytical condition 1), a purity of the objective compound 2'-O-acetyl-4"-O-formyl-8,9-anhydroerythromycin A 6,9-hemiketal (Compound 4) was 87.0% (areal percentage). Incidentally, an existence ratio of Compound 4 and a by-product (11-O-formyl-2'-O-acetyl-4"-O-formyl-8,9-anhydroerythromycin A 6,9-hemiketal) was 95.6:4.3.

Incidentally, when the resulting material was analyzed by high performance liquid chromatography (an internal standard method, analytical condition 1) using crystals of Compound 4 obtained in Example 1 as 100%, a content of Compound 4 in the above-mentioned crystals was 80%.

Incidentally, analytical conditions of high performance liquid chromatography in the above-mentioned Examples, Reference examples and Comparative examples are as follows.

Analytical Condition 1

Column: Kromasil KR100-5C18
Column temperature: 30° C.
Eluent: Acetonitrile/water/28% aqueous ammonia (=700/300/3
(Volume ratio))
Flow rate: 1.0 ml/min.
Detection wavelength: 215 nm Analytical condition 2

Column: L-column ODS
Column temperature: 25° C.
Eluent: Acetonitrile/water/28% aqueous ammonia (=725/275/40
(Volume ratio))
Flow rate: 1.0 ml/min.
Detection wavelength: 215 nm

UTILIZABILITY IN INDUSTRY

According to the present invention, starting from 2'-O-acetylerythromycin a compound, a process for preparing an erythromycin compound industrially suitable which realizes obtaining a 2'-O-acetyl-4"-O-formyl-8,9-anhydroerythromycin A 6,9-hemiketal compound (compound 4) having high purity and containing substantially no by-product (11-O-formyl-2'-O-acetyl-4"-O-formyl-8,9-anhydroerythromycin A 6,9-hemiketal) as crystals.

What is claimed is:
1. A process for producing an erythromycin compound which is a 2'-O-acetyl-4"-O-formyl-8,9-anhydroerythromycin A 6,9-hemiketal compound 4 represented by the formula (4):

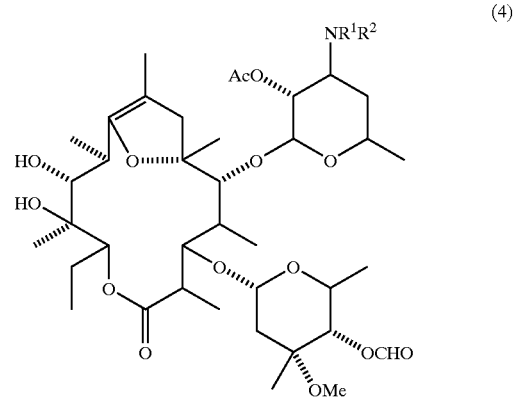

wherein $R^1$ and $R^2$ each independently represent a lower alkyl group,
which comprises reacting a 2'-O-acetylerythromycin A compound 2 represented by the formula (2):

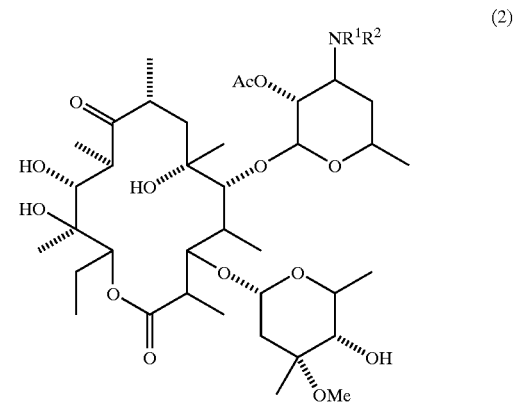

wherein $R^1$ and $R^2$ have the same meanings as defined above,
with a formylating agent to obtain a 2'-O-acetyl-4"-O-formylerythromycin A compound 3 represented by the formula (3):

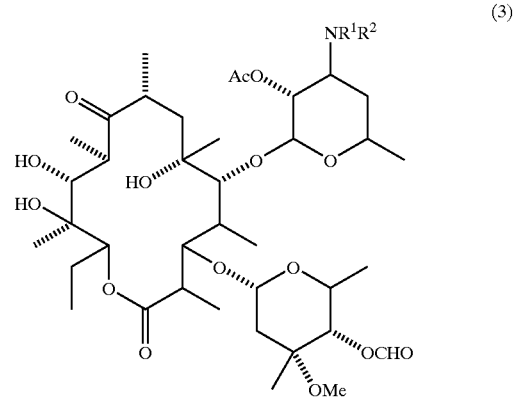

wherein $R^1$ and $R^2$ have the same meanings as defined above,
then, reacting Compound 3 with an acid to subject to hemiketalation, and adding an aqueous basic solution in an aqueous solution to precipitate Compound 4 as free crystals.

2. The preparation process according to claim 1, wherein the process further comprises a step of reacting an acetylating agent to the erythromycin A compound 1 represented by the formula (1):

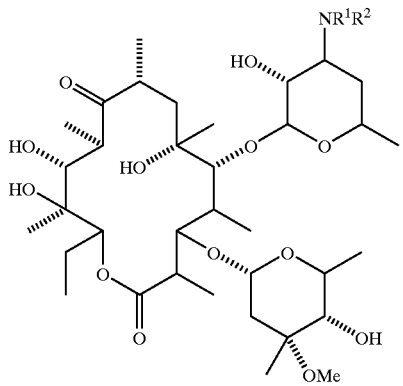

wherein $R^1$ and $R^2$ each independently represent a lower alkyl group,
to obtain Compound 2 before reacting the formylating agent with Compound 2 in the process according to claim 1.

3. The preparation process according to claim 2, wherein after reacting with the acetylating agent, the obtained Compound 2 is reacted with the formylating agent continuously without subjecting to isolation and purification hereof.

4. The preparation process according to any one of claims 1 to 3, wherein after reacting with the formylating agent, the obtained Compound 3 is subjected to hemiketalation continuously without subjecting to isolation and purificaion thereof.

5. The preparation process according to claim 1 wherein after subjecting to hemiketalation, an aqueous basic solution is added to a reaction mixture to make a pH of the reaction mixture to 6.5 to 10.0.

6. The preparation process according to claim 1 wherein $R^1$ and $R^2$ are each a methyl group.

7. The preparation process according to claim 1 wherein $R^1$ is a methyl group, and $R^2$ is an isopropyl group.

8. The preparation process according to claim 1 wherein the formylating agent is selected from the group consisting of a mixture of formic acid-acetic acid compound and 1-formylimidazole.

9. The preparation process according to claim 1 wherein the formylating agent is selected from the group consisting of formic acid-acetic anhydride, sodium formate-acetyl chloride and 1-formylimidazole.

10. The preparation process according to claim 1 wherein the formylating agent is selected from the group consisting of formic acid-acetic anhydride and sodium formate-acetyl chloride.

11. The preparation process according to claim 2, wherein the acetylating agent is selected from the group consisting of an acetic anhydride, an acetyl halide, an acetate and 1-acetylimidazole.

12. The preparation process according to claim 2 wherein the acetylating agent is selected from the group consisting of acetic anhydride, acetyl chloride, sodium acetate and 1-acetylimidazole.

13. The preparation process according to claim 2 wherein the acetylating agent is selected from the group consisting of acetic anhydride and acetyl chloride.

14. A process for isolating and purifying a 2'-O-acetyl-4"-O-formyl-8,9-anhydroerythromycin A 6,9-hemiketal compound represented by the formula (4):

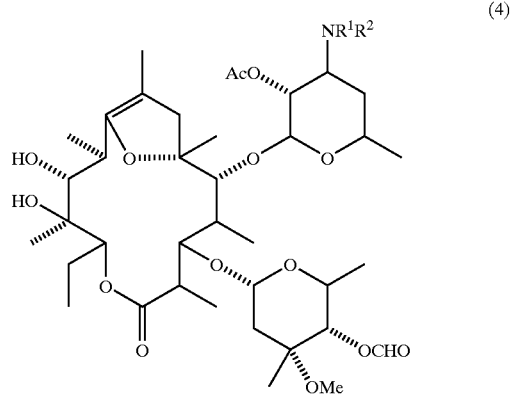

wherein $R^1$ and $R^2$ each independently represent a lower alkyl group,
wherein the preparation process comprises adding a basic solution to an aqueous solution containing the compound and impurities to precipitate the compound from the aqueous solution as free crystals.

* * * * *